US 9,213,007 B2

(12) United States Patent
Matoba

(10) Patent No.: US 9,213,007 B2
(45) Date of Patent: Dec. 15, 2015

(54) FOREIGN MATTER DETECTOR

(71) Applicant: Hitachi High-Tech Science Corporation, Minato-ku, Tokyo (JP)

(72) Inventor: Yoshiki Matoba, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 86 days.

(21) Appl. No.: 14/224,437

(22) Filed: Mar. 25, 2014

(65) Prior Publication Data

US 2014/0294144 A1 Oct. 2, 2014

(30) Foreign Application Priority Data

Mar. 28, 2013 (JP) ................................. 2013-068421

(51) Int. Cl.
*G01N 23/223* (2006.01)
(52) U.S. Cl.
CPC ..................... *G01N 23/223* (2013.01)
(58) Field of Classification Search
CPC .......... G01N 23/223; G01N 2223/076; G01N 23/2204; G01N 23/2206; G01N 2223/652
See application file for complete search history.

(56) References Cited

U.S. PATENT DOCUMENTS

| 2013/0034204 A1* | 2/2013 | Matoba et al. ................ 378/44 |
| 2013/0039460 A1* | 2/2013 | Levy et al. .................... 378/44 |
| 2013/0121460 A1* | 5/2013 | Mitsunaga et al. ............ 378/44 |

FOREIGN PATENT DOCUMENTS

JP 2013-036793 A 2/2013

* cited by examiner

*Primary Examiner* — Hoon Song
(74) *Attorney, Agent, or Firm* — Banner & Witcoff, Ltd.

(57) ABSTRACT

A foreign matter detector includes an X-ray source which irradiates a sample moving in a constant direction with primary X-rays, a parallel two-dimensional slit which includes a plurality of slits arranged in at least a moving direction of the sample and emits parallel secondary X-rays by extracting a parallel component of secondary X-rays generated from the sample, a dispersing element which disperses the parallel secondary X-rays to obtain a specific X-ray fluorescence, a TDI sensor which receives the X-ray fluorescence, and a control unit which controls the TDI sensor to detect a foreign matter corresponding to the X-ray fluorescence. The control unit integrates a luminance value of the X-ray fluorescence received by the TDI sensor while matching a direction and a speed of charge transfer of the TDI sensor to a direction and a speed of movement of the sample.

5 Claims, 1 Drawing Sheet

FOREIGN MATTER DETECTOR

CROSS-REFERENCE TO RELATED APPLICATION

This application claims priority from Japanese Patent Application No. 2013-068421, filed on Mar. 28, 2013, the entire subject matter of which is incorporated herein by reference.

TECHNICAL FIELD

The present invention relates to a foreign matter detector capable of detecting a specific foreign metal matter contained in a continuously moving sample, and particularly, capable of detecting a specific foreign metal matter contained in a fluid sample such as a continuously flowing powder or liquid, or a sample of a thin-plate or a foil form which is continuously moving.

BACKGROUND

Generally, an X-ray transmission inspection is used as a method of detecting a foreign metal matter in a sample. However, in some cases, an element of the foreign matter cannot be specified by this inspection, and a main component, which is not a foreign matter, is wrongly detected as a foreign matter.

Further, an X-ray fluorescence analysis is known as a method of analyzing an element of a sample. In the X-ray fluorescent analysis, the sample is irradiated with X-rays emitted from an X-ray source, and an X-ray fluorescence, which is characteristic X-rays emitted from the sample, is detected by an X-ray detector. Accordingly, a qualitative analysis or a quantitative analysis of the sample is performed based on spectrums obtained from the generated energy. Since the X-ray fluorescence analysis can analyze the sample quickly and in a nondestructive manner, this analysis is widely used in a process and quality control.

For example, JP-A-2013-36793 discloses an X-ray analyzer which integrates an X-ray transmission inspection and the X-ray fluorescent analysis so as to perform a detection and elemental analysis of a foreign matter in a sample. This analyzer includes an X-ray transmission inspection unit and an X-ray fluorescence inspection unit. The X-ray transmission inspection unit detects the foreign matter in the sample and specifies a position thereof, and applies primary X-rays radiated from the X-ray fluorescence inspection unit to the position of the detected foreign matter, so that an accurate elemental analysis of a foreign matter can be performed.

SUMMARY

In the above-described device has the following problems.

That is, any of related-art foreign matter detecting methods detects foreign matters by X-ray irradiation in a state where a sample such as a powder is stationary. Therefore, it is difficult to detect only a specific foreign metal matter in a state where a powder such as a carbon and a metal flows with an air at a constant speed. For example, during the process in which a carbon black for a lithium ion battery, a material such as a positive electrode active material, a pharmaceutical powder, and the like flow at a constant speed, it is not possible to detect the contained foreign matter without stopping the flow. In other words, since the sample such as a powder to be measured is not fixed and flows to be moved through the irradiation region of primary X-rays in short time, there is a problem in that the amount of the detected secondary X-rays obtained from the foreign matter is small, and the influence of the secondary X-rays from elements other than the foreign matter increases, so that the sensitivity to the information about the X-ray fluorescence from the foreign matter is insufficient.

The present invention has been made in view of the above-described circumstances, and an object of the present invention is to provide a foreign matter detector capable of detecting a specific foreign metal matter contained in a fluid sample such as a continuously flowing powder or liquid, or a sample of a thin-plate or a foil form which is continuously moving.

According to an illustrative embodiment of the present invention, there is provided a foreign matter detector comprising: an X-ray source which is configured to irradiate a sample moving in a constant direction with primary X-rays; a parallel two-dimensional slit which includes a plurality of slits arranged in at least a moving direction of the sample and is configured to emit parallel secondary X-rays by extracting a parallel component of secondary X-rays generated from the sample irradiated with the primary X-rays; a dispersing element which is configured to disperse the parallel secondary X-rays to obtain a specific X-ray fluorescence; a Time Delay Integration (TDI) sensor which is configured to receive the X-ray fluorescence; and a control unit which is configured to control the TDI sensor to detect a foreign matter corresponding to the X-ray fluorescence, wherein the control unit is configured to integrate a luminance value of the X-ray fluorescence received by the TDI sensor while matching a direction and a speed of charge transfer of the TDI sensor to a direction and a speed of movement of the sample.

In the foreign matter detector, the control unit integrates a luminance value of the X-ray fluorescence received by the TDI sensor while matching the direction and speed of charge transfer of the TDI sensor to the direction and speed of movement of the sample. Therefore, detection of the X-ray fluorescence of the foreign matter can be performed with a good S/N while the influence of secondary X-rays (X-ray fluorescence and scattered X-ray) from an element other than the foreign matter is minimized.

In the above foreign matter detector, the sample may be a fluid sample flowing in a constant direction or a sample of a thin-plate or a foil form which is moving in a constant direction.

That is, in the foreign matter detector, since a sample is the fluid sample flowing in the constant direction or the sample of the thin-plate or the foil form which is moving in the constant direction, it is possible to detect a foreign matter from the flowing fluid sample or the sample of the thin-plate or the foil form which is moving, with high sensitivity by matching the direction and speed of charge transfer of the TDI sensor to the direction and speed of movement of the fluid sample or the sample of the thin-plate or foil form.

In the above foreign matter detector, the parallel two-dimensional slit may include a poly-capillary.

The above foreign matter detector may further comprise a speed sensor which is configured to measure a moving speed of the sample, wherein the control unit may be configured to control the TDI sensor based on the moving speed of the sample measured by the speed sensor.

That is, in the foreign matter detector, the control unit controls the TDI sensor based on the moving speed of the sample which is detected by the speed sensor, so that it is possible to control the TDI sensor based on the correct speed of the sample, and thus to obtain a higher sensitivity.

In the above foreign matter detector, the dispersing elements may include a plurality of dispersing elements in which incidence angles of the parallel secondary X-rays are different from each other, and the TDI sensor may include a plurality of TDI sensors provided correspondingly to the plurality of dispersing elements.

That is, in the foreign matter detector, the plurality of dispersing elements in which incident angles of the parallel secondary X-rays are different from each other are provided, and the plurality of TDI sensors are provided correspondingly to the plurality of dispersing elements. Therefore, the plurality of dispersing elements and TDI sensors are made to correspond to foreign matters of a plurality of elements which are different from each other, and thus it is possible to simultaneously detect foreign matters of the plurality of elements from the flowing sample.

According to the above configuration, the following effects may be obtained.

That is, according to the above-described foreign matter detector, the control unit integrates a luminance value of the X-ray fluorescence received by the TDI sensor while matching the direction and speed of charge transfer of the TDI sensor to the direction and speed of movement of the sample. Therefore, detection of the X-ray fluorescence of the foreign matter can be performed with a good S/N while the influence of secondary X-rays (X-ray fluorescence and scattered X-ray) from an element other than the foreign matter is minimized. Therefore, if the foreign matter detector is used, during the process in which a carbon black for a lithium ion battery, materials such as a positive electrode active material, a pharmaceutical powder, and the like flow at a constant speed, or during a process in which a cobalt oxide lithium electrode plate and the like used in the positive electrode of the lithium ion battery moves in a certain speed, it is possible to detect with high sensitivity the contained foreign matter without stopping the process.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Hereinafter, a foreign matter detector according to a first illustrative embodiment of the present invention will be described with reference to FIG. 1.

Figure 1:
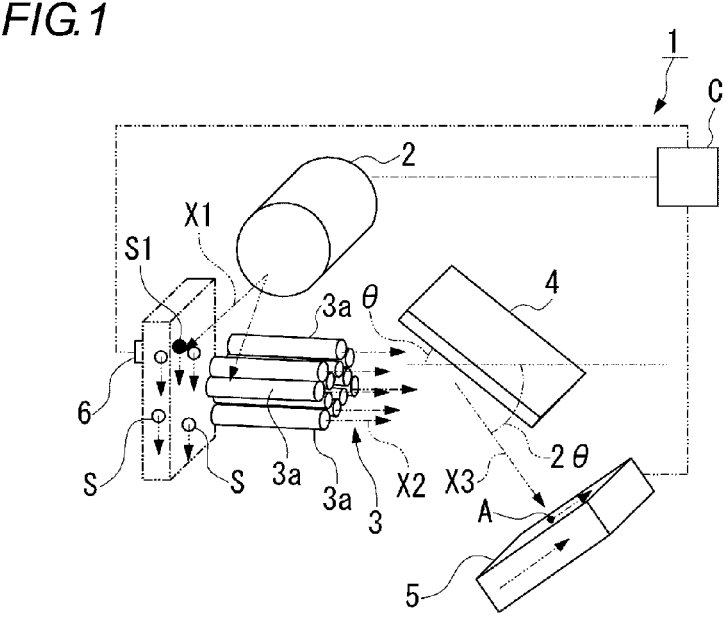
FIG. 1 is an overall configuration diagram schematically showing a foreign matter detector according to a first illustrative embodiment of the present invention.

As shown in FIG. 1, the foreign matter detector 1 of the first illustrative embodiment includes an X-ray source 2 which irradiates a sample S moving in a constant direction with primary X-rays X1, a parallel poly-capillary 3 including a plurality of capillaries 3a arranged in at least a moving direction of the sample S and emits parallel secondary X-rays X2 while extracting a parallel component of a part of secondary X-rays X2 generated from the sample S which is irradiated with the primary X-rays X1, a dispersing element 4 which disperses the parallel secondary X-rays X2 to obtain a specific X-ray fluorescence X3, a Time Delay Integration (TDI) sensor 5 which receives the X-ray fluorescence X3, and a control unit C which controls the TDI sensor 5 to detect the foreign matter 51 corresponding to the X-ray fluorescence X3.

The control unit C integrates a luminance value of the X-ray fluorescence X3 received by the TDI sensor 5 while matching the direction and speed of charge transfer of the TDI sensor 5 to the direction and speed of movement of the sample S.

Further, the foreign matter detector 1 of the first illustrative embodiment includes a speed sensor 6 which measures the moving speed of the sample S. For example, an electromagnetic flow meter which is a flow rate sensor or the like is employed as the speed sensor 6. Incidentally, when the moving speed of the sample S is constant and can be recognized accurately, the speed sensor 6 may be removed.

The control unit C controls the TDI sensor 5 based on the moving speed of the sample S measured by the speed sensor 6.

The sample S is a fluid sample of a powder or a liquid which flows in a constant direction. The sample S flows to be transferred from a flow path along which carbon or metal powders flow at a constant speed with an air to a plane flow path having a relatively thin thickness. The sample S flowing through the plane flow path is irradiated with the primary X-rays X1 emitted from the X-ray source 2.

The X-ray source 2 is an X-ray tube capable of emitting primary X-rays. Specifically, the X-ray source 2 emits from the window such as beryllium foil, as the primary X-rays X1, X-rays which are generated by collision of thermo electrons generated between a filament (cathode) inside the tube and accelerated by a voltage applied between the filament (cathode) and a target (anode), with the W (tungsten), MO (molybdenum), Cr (Chromium) of the target.

The parallel poly-capillary 3 includes a bundle of capillaries (slits) 3a which are glass tubes having a diameter of about 10 μm, and has a function as a parallel two-dimensional slit which extracts only a parallel component by causing the radially generated secondary X-rays to be incident from a based end to be totally reflected in the inside, and emits the extracted parallel component from a tip end. Each capillary 3a functions as an X-ray slit which extracts only a parallel component by causing the secondary X-rays to be incident from the base end and to be totally reflected in the inside. In the parallel poly-capillary 3, capillaries 3a are arranged and extended in the direction perpendicular to the moving direction of the sample S. Since the plurality of capillaries 3a are arranged also in the direction along the moving direction of the sample S, the secondary X-rays emitted by the moving foreign matter 51 can be incident thereto.

The dispersing element 4 is made from a single crystal of lithium fluoride or germanium which disperses (diffracts) the parallel secondary X-rays. The single crystal of the dispersing element 4 disperses the incident secondary X-rays X2 with an incidence angle (diffraction angle) of θ to obtain X-ray fluorescence X3 with a dispersion angle 2θ which is double the incidence angle θ so as to be emitted, based on the following Bragg's equation.

$$2d \cdot \sin \theta = n\lambda d \qquad \text{Bragg's equation}$$

(where, d: a crystal spacing of the dispersing element 4, n: a diffraction order, and λ: a wavelength of X-ray fluorescence)

The TDI sensor 5 includes a plurality of lines of CCDs which are arranged two-dimensionally, i.e. vertically and horizontally, and has a configuration in which a plurality of line sensors are arranged.

The TDI sensor 5 is disposed at a position corresponding to the dispersion angle satisfying the Bragg's equation such that a light receiving surface is perpendicular to the incident X-ray fluorescence X3. In other words, the TDI sensor 5 is disposed at a position where the X-ray fluorescence X3 due to a specific element, among secondary X-rays X2 which are incident to the single crystal of the dispersing element 4 with an incidence angle θ, may interfere with (be diffracted in) the single crystal and emits with the specific dispersion angle 2θ. In this manner, the TDI sensor 5 is disposed in a direction in which the X-ray fluorescence X3 emitted from the element of the foreign matter S1 desired to be detected diffract in the dispersing element 4 to be emitted.

The control unit C is connected to the X-ray source 2, the TDI sensor 5, and the like, and is a computer which includes a CPU for controlling them.

The control unit C sets the speed of charge transfer of the TDI sensor 5 (feed speed) $V_{TDI}$ same as the speed $V_s$ of the sample S, and controls the flow of the sample S and the integration process of the TDI sensor 5 to be synchronized with each other.

Subsequently, a foreign matter detection method using the foreign matter detector 1 of the first illustrative embodiment will be described.

First, the X-ray source 2 irradiates a part of the sample S flowing along the plane flow path with the primary X-rays X1. At this time, secondary X-rays such as the X-ray fluorescence and the scattered X-ray are radially generated from powders of the main component and the foreign metal matter S1 in the flowing sample S.

The parallel poly-capillary 3 disposed perpendicularly to the parallel plane of the plane flow path extracts only a parallel component of a part of the generated secondary X-rays, and input the parallel secondary X-rays X2 to the dispersing element 4.

The dispersing element 4 diffracts the incident parallel secondary X-rays X2 with the dispersion angle satisfying the Bragg's equation. In other words, only the X-ray fluorescence X3 from the element of the foreign matter S1 desired to be detected are diffracted at a predetermined diffraction angle, and thus appears as a bright point A in the TDI sensor 5 disposed at a predetermined position. At this time, since the foreign matter S1 of the sample S moves, a capillary 3a, into which the secondary X-rays from the foreign matter S1 which are incident to the parallel poly-capillary 3 is mainly incident, also changes from the capillary 3a on the upstream to the capillary 3a on the downstream.

Therefore, the bright point A of the X-ray fluorescence X3 diffracted in the dispersing element 4 and received by the TDI sensor 5 moves in the same way. The control unit C controls the TDI sensor 5 so as to match the direction and speed of charge transfer of the TDI sensor 5 to the direction and speed of flow (movement) of the sample S, and thus the charges generated at the moving bright point A are integrated by being subjected to an integration exposure in the movement direction. Therefore, since the bright point A which moves along with the movement of the foreign matter S1 is integrated, it is possible to obtain a high sensitivity even if the bright point A is a low luminance.

Accordingly, in the foreign matter detector 1 of the first illustrative embodiment, the control unit C integrates a luminance value of the X-ray fluorescence X3 received by the TDI sensor 5 while matching the direction and speed of charge transfer of the TDI sensor 5 to the direction and speed of movement of the sample S. Therefore, detection of the X-ray fluorescence X3 of the foreign matter S1 can be performed with a favorable S/N while the influence of secondary X-rays (X-ray fluorescence and scattered X-ray) from an element other than the foreign matter S1 is minimized.

Further, the control unit C controls the TDI sensor 5 based on the speed of the sample S which is detected by the speed sensor 6, so that it is possible to control the TDI sensor 5 based on the correct speed of the sample S, thereby obtaining a higher sensitivity.

Subsequently, a foreign matter detector according to a second illustrative embodiment of the present invention will be described with reference to FIG. 2. In the description of the second illustrative embodiment, the same components as the components described in the first illustrative embodiment are denoted by the same reference numerals, and thus a description thereof will be omitted.

Figure 2:
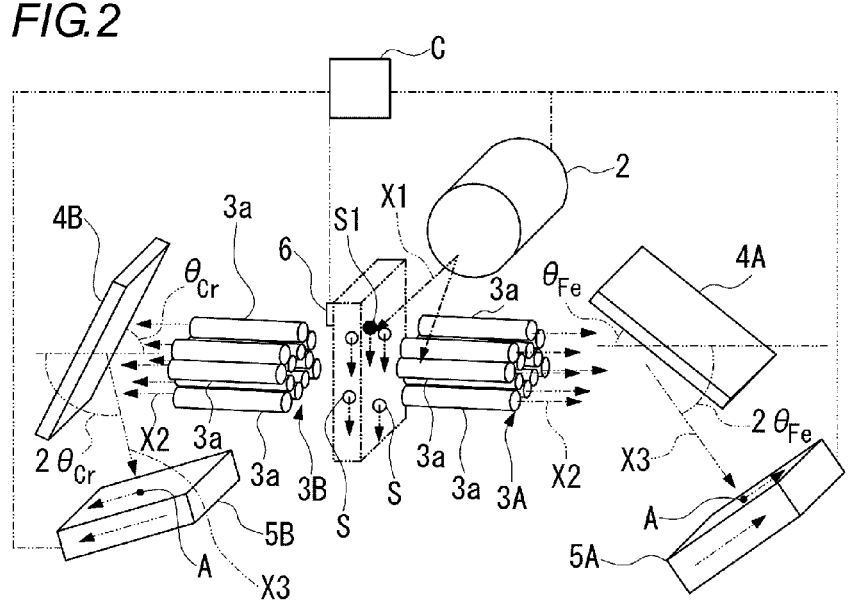
FIG. 2 is an overall configuration diagram schematically showing a foreign matter detector according to a second illustrative embodiment of the present invention.

The second illustrative embodiment is different from the first illustrative embodiment in that one parallel poly-capillary 3, one dispersing element 4 and one TDI sensor 5 are provided to detect the foreign matter S1 of one element in the first illustrative embodiment, whereas two dispersing elements 4A and 4B in which incidence angles of the parallel secondary X-rays X2 are different from each other are provided to detect the foreign matters S1 of two different elements and two TDI sensors 5A and 5B are provided correspondingly to the two dispersing elements 4 in the foreign matter detector 21 of the second illustrative embodiment, as shown in FIG. 2.

In other words, in the second illustrative embodiment, a pair of parallel poly-capillaries 3A and 3B, a pair of dispersing elements 4A and 4B and a pair of TDI sensors 5A and 5B are provided on both sides of the flowing sample S. For example, the parallel poly-capillary 3A, the dispersing element 4A and the TDI sensor 5A on one side are a mechanism which detects the Fe element, and the parallel poly-capillary 3B, the dispersing element 4B and the TDI sensor 5B on the other side are a mechanism which detects the Cr element.

In the second illustrative embodiment, the secondary X-rays generated from the sample S by the primary X-rays X1 applied to the sample S flowing along the plane flow path are emitted radially to both sides of the plane flow path.

The dispersing element 4A and the TDI sensor 5A on one side are set at an inclination and a position corresponding to an inclination angle $\theta_{Fe}$ and a diffraction angle $2\theta_{Fe}$ to detect the Fe element. Further, the dispersing element 4B and the TDI sensor 5B on the other side are set at an inclination and a position corresponding to an inclination angle $\theta_{Cr}$ and a diffraction angle $2\theta_{Cr}$ to detect the Cr element.

That is, the plurality of dispersing elements 4A and 4B in which incidence angles of the parallel secondary X-rays X2 are different from each other are provided and the plurality of TDI sensors 5A and 5B are provided correspondingly to the plurality of dispersing elements 4A and 4B in the foreign matter detector 21 of the second illustrative embodiment. If the plurality of dispersing elements 4A and 4B and the TDI sensors 5A and 5B are made correspond to foreign matters S1 of a plurality of elements which are different from each other, it is possible to simultaneously detect the foreign matters S1 of the plurality of elements in the flowing sample S.

While the present invention has been shown and described with reference to certain illustrative embodiments thereof, it will be understood by those skilled in the art that various changes in form and details may be made therein without departing from the spirit and scope of the invention as defined by the appended claims.

For example, although a fluid sample such as a flowing power or a liquid is used as a measurement sample in the above illustrative embodiments, a sample of a thin-plate or foil form moving in a constant direction may be used as a sample of a foreign matter inspection object. For example, during a process in which a cobalt oxide lithium electrode plate and the like used in the positive electrode of the lithium ion battery moves in a constant speed, the foreign matter detector may be used in detecting foreign matter contained in the cobalt oxide lithium electrode plate.

What is claimed is:

1. A foreign matter detector comprising:
an X-ray source which is configured to irradiate a sample moving in a constant direction with primary X-rays;
a parallel two-dimensional slit which includes a plurality of slits arranged in at least a moving direction of the sample and is configured to emit parallel secondary X-rays by extracting a parallel component of secondary X-rays generated from the sample irradiated with the primary X-rays;
a dispersing element which is configured to disperse the parallel secondary X-rays to obtain a specific X-ray fluorescence;
a Time Delay Integration (TDI) sensor which is configured to receive the X-ray fluorescence; and
a control unit which is configured to control the TDI sensor to detect a foreign matter corresponding to the X-ray fluorescence,
wherein the control unit is configured to integrate a luminance value of the X-ray fluorescence received by the TDI sensor while matching a direction and a speed of charge transfer of the TDI sensor to a direction and a speed of movement of the sample.

2. The foreign matter detector according to claim 1, wherein the sample is a fluid sample flowing in a constant direction or a sample of a thin-plate or a foil form which is moving in a constant direction.

3. The foreign matter detector according to claim 1, wherein the parallel two-dimensional slit includes a polycapillary.

4. The foreign matter detector according to claim 1, further comprising:
a speed sensor which is configured to measure a moving speed of the sample,
wherein the control unit is configured to control the TDI sensor based on the moving speed of the sample measured by the speed sensor.

5. The foreign matter detector according to claim 1, wherein the dispersing elements includes a plurality of dispersing elements in which incidence angles of the parallel secondary X-rays are different from each other, and
wherein the TDI sensor includes a plurality of TDI sensors provided correspondingly to the plurality of dispersing elements.

* * * * *